United States Patent
Howard, Jr. et al.

(10) Patent No.: US 9,505,667 B2
(45) Date of Patent: Nov. 29, 2016

(54) METHOD FOR PREPARING DEUTERATED AROMATIC COMPOUNDS

(71) Applicant: E I DU PONT DE NEMOURS AND COMPANY, Wilmington, DE (US)

(72) Inventors: Michael Henry Howard, Jr., Montchanin, DE (US); David P Bellon, Wilmington, DE (US); David P Dickson, Merion Station, PA (US); Jeffrey A Merlo, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/534,299

(22) Filed: Nov. 6, 2014

(65) Prior Publication Data

US 2016/0130194 A1    May 12, 2016

(51) Int. Cl.
*C07D 487/04* (2006.01)
*C07B 59/00* (2006.01)
*C07D 251/42* (2006.01)

(52) U.S. Cl.
CPC ........... *C07B 59/002* (2013.01); *C07D 251/42* (2013.01); *C07D 487/04* (2013.01)

(58) Field of Classification Search
CPC .......................... C07D 251/42; C07D 487/04
USPC ........................................................ 544/194
See application file for complete search history.

(56) References Cited

U.S. PATENT DOCUMENTS 7,517,990 B2 * 4/2009 Ito et al. ................... 546/184
8,093,422 B2 * 1/2012 Ito et al. ................... 562/493

FOREIGN PATENT DOCUMENTS

JP   2014-111561 A  *  6/2014
WO  2010114583 A1    10/2010
WO  2011043254 A1    4/2011

OTHER PUBLICATIONS

Sajiki et al., CAPLUS Abstract 161:86101 (2014)—English Abstract of JP 2014-111561A, Jun. 19, 2014.*
English (machine) Translation of WO 2011/043254 A1 (2011).*
Browne__RoutesToRegioselectiveDeuteration__InorganicChem__2002_vol. 41_pp. 4245-4251.
Browne__DeuterationPhenanthroline__InorganicChem__2002_vol. 41_pp. 4245-4251_SupportingInformation.
Atzrodt__TheRenaissanceOfH-DExchange__ChemIntEd__2007_vol. 46_pp. 7744-7765.
Atzrodt__Pd-AndPt-CatalyzedH-DExchangeMethods__LabelledCompounds__2010_vol. 53_pp. 674-685.
Proszenyak__ConvenientMethodsForTheSynthesisOf__LabelledCompounds__2005_vol. 48_pp. 421-427.
Tong__EnhancementOLEDEfficiencies__JPhysChem__2007_pp. 3490-3494.
Darwish__DeuterationOfConjugatedAromaticHeterocycles__TetrahedronLetters__2011_vol. 53_pp. 931-935.
Matsubara__PlatinumCatalyzedH-DExchangeReaction__Heterocycles__2006_vol. 67_pp. 353-359.

* cited by examiner

*Primary Examiner* — Deepak Rao

(57) ABSTRACT

There is provided a method for deuterating an aromatic compound having aromatic hydrogens. The method includes the steps:
  (a) providing a liquid composition including deuterium oxide having dissolved or dispersed therein the aromatic compound and a transition metal catalyst; and
  (b) heating the liquid composition at a temperature of 120° C. or greater, and a pressure of 50 psi or greater, for a period of 24 hours or less, to form a deuterated aromatic compound.

13 Claims, No Drawings

METHOD FOR PREPARING DEUTERATED AROMATIC COMPOUNDS

BACKGROUND INFORMATION

Field of the Disclosure

This disclosure relates in general to methods for preparing deuterated aromatic compounds.

Description of the Related Art

Deuterium has a natural abundance of approximately 0.015%. Deuterated compounds, in which the level of deuterium is enriched, are well known. Deuterated aromatic compounds have been used to study chemical reactions and metabolic pathways. They also have uses as raw materials for pharmaceuticals, agricultural chemicals, functional materials, and analytical tracers. Certain deuterated electroluminescent materials exhibit improved performance (efficiency, lifetime) relative to their non-deuterated isotopologues (see, for example, Lecloux, et al. PCT Int. Appl. (2010), WO 2010114583 A1 20101007 and Tong, et al. *J. Phys. Chem. C* 2007, 111, 3490-4). Current methods of forming deuterated compounds can require multiple treatments in order to achieve high levels of deuteration. In addition, such methods can be costly and/or time consuming.

There is a continuing need for improved methods for forming deuterated aromatic compounds.

SUMMARY

There is provided a method for deuterating an aromatic compound having aromatic hydrogens, said method comprising:
 (a) providing a liquid composition comprising deuterium oxide having dissolved or dispersed therein the aromatic compound and a transition metal catalyst; and
 (b) heating the liquid composition at a temperature of 120° C. or greater, and a pressure of 50 psi or greater, for a period of 24 hours or less, to form a deuterated aromatic compound.

The foregoing general description and the following detailed description are exemplary and explanatory only and are not restrictive of the invention, as defined in the appended claims.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Method of Deuteration, and finally Examples.
1. Definitions and Clarification of Terms Before addressing details of embodiments described below, some terms are defined or clarified.

As used herein, the term "aromatic compound" is intended to mean an organic compound comprising at least one unsaturated cyclic group having 4n+2 delocalized pi electrons. The term is intended to encompass both hydrocarbon aromatic compounds and heteroaromatic compounds. The terms "hydrocarbon aromatic ring" or "hydrocarbon aromatic compound" refer to an aromatic ring or compound in which the aromatic moieties have only carbon and hydrogen atoms. The terms "heteroaromatic ring" or "heteroaromatic compound" refer to an aromatic ring or compound wherein in at least one aromatic moiety one or more of the carbon atoms within the cyclic group has been replaced by another atom, such as nitrogen, oxygen, sulfur, or the like.

The term "aromatic hydrogen" refers to a hydrogen directly bonded to an aromatic ring.

The term "deuterated" refers to a compound or group in which deuterium ("D") is present in at least 100 times the natural abundance level. By "deuteration" as it refers to a method, is meant to replace one or more hydrogens in a molecule with deuterons. By "% deuterated" or "% deuteration" is meant the ratio of deuterons to the sum of protons plus deuterons, expressed as a percentage.

The term "isotopologues" refers to molecules that differ only in their isotopic composition.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise. Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Method of Deuteration

There are two general strategies to produce deuterated materials. The first is multi-step synthesis from available deuterated precursor molecules. The limited structural diversity and relative high cost of commercially available deuterated precursors and reagents make this approach less desirable in most cases. The second general strategy is post-synthesis hydrogen-deuterium exchange. For a broad summary of H/D exchange methods, see Atzrodt, et al. *Angew. Chem. Int. Ed.* 2007, 46, 7744-65.

Synthetic methodologies that can be used to accomplish perdeuteration of C—H bonds fall into three categories: 1) acid- or base-treatment, 2) supercritical heating, and 3) transition metal-catalysis. Combinations of these methodologies, such as supercritical heating in the presence of base, are also used.

All three of these reaction types require a source of deuterium for the H/D exchange. Commercially available organic solvents used as deuterium sources in H/D exchange reactions include acetone-$d_6$, DMSO-$d_6$, DMF-$d_7$, methanol-$d_4$ and, most commonly, benzene-$d_6$. These deuterated organic solvents are in most cases prepared from $D_2O$ (heavy water) and are very expensive, especially when the actual number of deuterium atoms being transferred to substrate is considered. From a cost perspective it is desirable to use the much cheaper $D_2O$.

Among the pH-dependent exchange methods, base promoted processes have a relatively narrow scope of utility, limited mostly to exchange α- to carbonyl groups and in benzylic positions. A wide variety of Brönsted and Lewis acids promote exchange in a variety of hydrocarbon aromatic compounds in the presence of deuterated solvents. The effectiveness of acid promoted methods decreases markedly in cases where the aromatic substrate is less electron-rich. There can also be an issue of regioselectivity in acid-promoted processes where the positions of exchange follow the reactivity pattern seen in classical electrophilic substitution reactions. This can make achieving high levels of deuteration difficult without resorting to drastic reaction conditions.

Supercritical heavy water undergoes H/D exchange with aromatic substrates but the requirement for very high temperatures (>374° C.) precludes reaction with compounds lacking high thermal stability.

Both homogeneous (soluble complexes of Ir, Pt, Rh, and Ru) and heterogeneous ($PtO_2$, Pt (black), Pt—C, $Pd(OH)_2$, $PdCl_2$, Pd—C) transition metal catalysts can make use of $D_2O$ as the deuterium source in H/D exchange processes. This results in cost savings relative to processes that require more expensive deuterated organic solvents.

As shown in the Example, the extent of H/D exchange in $D_2O$ under platinum catalysis is unexpectedly higher than that observed in the Comparative Example using strong acid in $C_6D_6$. This higher reactivity can also reduce the need for multiple treatments to achieve perdeuteration.

The new method for deuteration of an aromatic compound comprises:
(a) providing a liquid composition comprising deuterium oxide having dissolved or dispersed therein the aromatic compound and a transition metal catalyst; and
(b) heating the liquid composition at a temperature of 120° C. or greater, and a pressure of 50 psi or greater, for a period of 24 hours or less, to form a deuterated aromatic compound.

In some embodiments, the method results in a higher percentage of deuteration than prior art methods.

In some embodiments, the product deuterated aromatic compound is at least 50% deuterated.

In some embodiments, the product deuterated aromatic compound is at least 60% deuterated.

In some embodiments, the product deuterated aromatic compound is at least 70% deuterated.

In some embodiments, the product deuterated aromatic compound is at least 80% deuterated.

In some embodiments, the aromatic compound has at least one hydrocarbon aromatic ring.

In some embodiments, the compound has multiple hydrocarbon aromatic rings.

In some embodiments, the compound has no heteroaromatic rings.

In some embodiments, the aromatic compound has fused aromatic rings.

Examples of hydrocarbon aromatic compounds include, but are not limited to, benzene, naphthalene, anthracene, biphenyl, terphenyl, naphthacene, pentacene, phenanthrene, chrysene, pyrene, fluoranthene, fluorene, benzofluorene, triphenylene, tetrabenzanthracene, and substituted derivatives thereof.

In some embodiments, the hydrocarbon aromatic compound is selected from the group consisting of anthracene, biphenyl, chrysene, fluroene, pyrene, triphenylene, and substituted derivatives thereof.

In some embodiments, the aromatic compound has at least one heteroaromatic ring.

In some embodiments, the heteroaromatic ring is an N-heteroaryl compound having at least one ring atom which is N.

In some embodiments, the N-heteroaryl compound is selected from the group consisting of pyrrole, imidazole, purine, pyrazole, triazole, pyridine, pyrazine, pyrimidine, pyridazine, triazine, indole, indoloindole, carbazole, indolocarbazole, benzimidazole, imidazobenzimidazole, indazole, benzotriazole, triazolopyridine, quinoline, isoquinoline, quinazoline, quinoxaline, naphthyridine, phenanthroline, quinolinoquinolines, and substituted derivatives thereof.

In some embodiments, the N-heteroaryl compound is selected from the group consisting of benzimidazole, indolocarbazole, indoloindole, isoquinoline, phenanthroline, quinolone, and substituted derivatives thereof.

In some embodiments, the aromatic compound has one or more hydrocarbon aromatic rings and at least one heteroaromatic ring.

In some embodiments, the hydrocarbon aromatic rings are further substituted with one or more substituents. Exemplary substituent groups include, but are not limited to, alkyl groups, alkoxy groups, silyl groups, siloxane groups, aryl groups, aryloxy groups and amino groups.

In some embodiments, the heteroaromatic rings are further substituted with one or more substituents. Exemplary substituent groups include, but are not limited to those given above.

Transition metal catalysts are well known in the art.

In some embodiments, the transition metal catalyst is an elemental metal.

In some embodiments, the transition metal catalyst is a metal oxide.

In some embodiments, the transition metal catalyst is a metal complex compound.

In some embodiments, the transition metal catalyst is a combination of two or more catalysts.

In some embodiments, the transition metal catalyst is selected from the group consisting of Pd, Pt, Ir, Rh, Ru, oxides thereof, complexes thereof, and combinations thereof.

In some embodiments, the transition metal catalyst is selected from the group consisting of Pd, Pt, oxides thereof, complexes thereof, and combinations thereof.

In some embodiments, the transition metal catalyst is a platinum catalyst. Exemplary types of platinum catalysts include, but are not limited to finely divided platinum metal ("platinum black"), platinum metal on graphitized carbon at loadings of at least 2.5 wt. %, and finely divided platinum oxide, $PtO_2$ ("Adam's catalyst").

In the method, the aromatic compound and the transition metal catalyst are dispersed in $D_2O$ to form a liquid composition. The materials can be added in any order.

In some embodiments, the molar ratio of aromatic compound to platinum catalyst is in the range of $10^5$: 1; in some embodiments, $10^4$: 1; in some embodiments, 1000:1; in some embodiments, 500:1.

In some embodiments, the molar ratio of available hydrogens in the aromatic compound to deuterons is at least 1:1.5. For example, a mixture of 0.10 mole of an aromatic compound having ten available hydrogens with one mole of $D_2O$ would have a molar ratio of available hydrogens to deuterons of (0.1×10):(1×2), which is 1:2. In some embodiments, the molar ratio is in the range of 1:1.5 to 1:1000; in some embodiments, 1:1.8 to 1:500; in some embodiments, 1:2 to 1:200.

In some embodiments, an additional solvent may be present. The additional solvent may be added to improve the solubility or dispersibility of the aromatic compound, as long as the solvent does not adversely affect the deuteration of the aromatic compound.

In some embodiments, the additional solvent is an ether, alcohol, alkane, cycloalkane, acid, amide or ester. Examples of additional solvents include, but are not limited to THF, methanol, ethanol, isopropanol, acetic acid, N,N-dimethylformamide, benzene, toluene, xylene, mesitylene, cyclohexane, methylcyclohexane, and fused cyclic alkanes.

The liquid composition is then treated at elevated temperature and pressure.

In some embodiments, the liquid composition is treated at elevated temperature and pressure in an air atmosphere. By "air atmosphere" it is meant that no additional gasses, such as $H_2$ or $D_2$, are added to the mixture prior to or during the heating step. In some embodiments, the air is dried to remove water.

In some embodiments, the liquid composition is treated at elevated temperature and pressure in an inert gas atmosphere. By "inert gas" it is meant a gas or mixture of gases that does not react under the process conditions. Inert gases which can be used include, but are not limited to, nitrogen and the noble gases.

In some embodiments, the liquid composition is treated at elevated temperature and pressure in an atmosphere including $H_2$ gas.

In some embodiments, the liquid composition is treated at elevated temperature and pressure in an atmosphere including $D_2$ gas. In general, the composition can be placed in a container in the desired atmosphere, sealed, and heated to the desired temperature. Such methods are well known.

The temperature for step (b) is 120° C. or greater.

In some embodiments, the temperature is between 120° C. and 500° C.; in some embodiments, 150° C. and 400° C.; in some embodiments, 200° C. and 300° C.

The pressure for step (b) is 50 psi or greater.

In some embodiments, the pressure is in the range of 50-1000 psi; in some embodiments 200-800 psi; in some embodiments, 500-700 psi.

Step (b) is carried out for 24 hours or less.

In some embodiments, the aromatic compound is treated at elevated temperature and pressure for a period of 1-24 hours; in some embodiments, 2-15 hours; in some embodiments 3-10 hours.

After cooling and returning to atmospheric pressure, the deuterated material can be isolated using any known techniques. Such techniques include, but are not limited to, extraction, precipitation, filtration, evaporation, distillation, chromatography, and the like.

Any of the above embodiments of the new method can be combined with one or more of the other embodiments, so long as they are not mutually exclusive. For example, the embodiment in which the molar ratio of available hydrogens in the aromatic compound to deuterons is in the range of 1:1.5 to 1:1000 can be combined with the embodiment in which the temperature is between 200° C. and 300° C. The same is true for the other non-mutually-exclusive embodiments discussed above. The skilled person would understand which embodiments were mutually exclusive and would thus readily be able to determine the combinations of embodiments that are contemplated by the present application.

EXAMPLES

The concepts described herein will be further described in the following examples, which do not limit the scope of the invention described in the claims.

Example 1

This example illustrates the process of the invention with Compound 1, a heteroaromatic compound.

Compound 1 is shown below, where "Ph" represents phenyl:

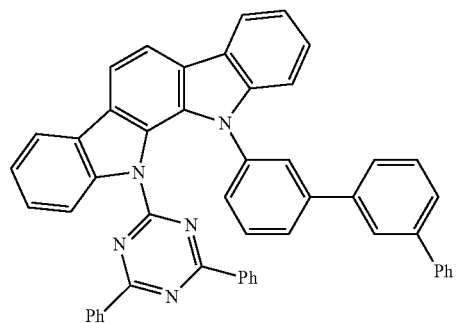

Compound 1

To a 200 mL shaker tube are added 7.16 g (10.0 mmol) of Compound 1, 700 mg (3.08 mmol) of PtO2, and 50 mL (55.35 g, 2763 mmol). The tube is sealed and heated at 250° C., 600 psi for 12 hours. The resulting product was dissolved in chloroform, filtered, and purified by column chromatography. Analysis by UPLC-MS showed the compound to be a mixture of isotopologues that were 82% deuterated.

Comparative Example A

Compound 1 (0.716 g, 1.0 mmol) was dissolved in d6-benzene (106 mL, 1,200 mmol). To this was added triflic acid (7.56 g, 50.0 mmol). The mixture was heated at 20° C. for 21 hours. The reaction was quenched with $K_3PO_4$ in $D_2O$. The organic layer was isolated, concentrated and purified by column chromatography on a silica column. The final mass was determined by UPLC-MS, which indicated the compound to be a mixture of isotopologues that were 52-55% deuterated.

It was also noted that when this reaction was carried out at higher temperatures, impurities were generated.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A method for deuterating an aromatic compound having aromatic hydrogens, said method comprising:
    (a) providing a liquid composition comprising deuterium oxide having dissolved or dispersed therein the aromatic compound and a transition metal catalyst; and
    (b) heating the liquid composition at a temperature of 120° C. or greater, and a pressure of 50 psi or greater, for a period of 24 hours or less, to form a deuterated aromatic compound;
    wherein (b) is carried out in an air atmosphere.

2. The method of claim 1, wherein the aromatic compound is a hydrocarbon aromatic compound.

3. The method of claim 2, wherein the hydrocarbon aromatic compound is selected from the group consisting of naphthalene, anthracene, biphenyl, terphenyl, naphthacene, pentacene, phenanthrene, chrysene, pyrene, fluoranthene, fluorene, benzofluorene, triphenylene, tetrabenzanthracene, and substituted derivatives thereof.

4. The method of claim 1, wherein the aromatic compound is an N-heteroaryl compound.

5. The method of claim 4, wherein the N-heteroaryl compound is selected from the group consisting of pyrrole, imidazole, purine, pyrazole, triazole, pyridine, pyrazine, pyrimidine, pyridazine, triazine, indole, indoloindole, carbazole, indolocarbazole, benzimidazole, imidazobenzimidazole, indazole, benzotriazole, triazolopyridine, quinoline, isoquinoline, quinazoline, quinoxaline, naphthyridine, phenanthroline, quinolinoquinolines, and substituted derivatives thereof.

6. The method of claim 1, wherein the transition metal catalyst is selected from the group consisting of Pd, Pt, Ir, Rh, Ru, oxides thereof, complexes thereof, and combinations thereof.

7. The method of claim 6, wherein the transition metal catalyst is a platinum catalyst selected from the group consisting of finely divided platinum metal, platinum metal on graphitized carbon at loadings of at least 2.5 wt. %, and finely divided platinum oxide.

8. The method of claim 1, wherein the molar ratio of available hydrogens in the aromatic compound to deuterons is in a range of 1:1.5 to 1:1000.

9. The method of claim 1, wherein the temperature is between 120° C. and 500° C.

10. The method of claim 1, wherein the pressure is in the range of 200-800 psi.

11. The method of claim 1, wherein (b) is carried out for a period of 3-10 hours.

12. The method of claim 1, wherein the deuterated aromatic compound is at least 50% deuterated.

13. The method of claim 1, wherein the deuterated aromatic compound is at least 70% deuterated.

* * * * *